US005583265A

United States Patent [19]

Woo et al.

[11] Patent Number: 5,583,265

[45] Date of Patent: Dec. 10, 1996

[54] ACIDIC LIQUID DETERGENT COMPOSITIONS FOR BATHROOMS

[76] Inventors: Ricky A.-M. Woo, Sharon Woods Technical Center, 11520 Reed Hartman Hwy., Cincinnati, Ohio 45241-2422; Michel J. Carrie, Procter & Gamble European Technical Center, Temselaan 100, B 1853 Strombeek-Bever, Belgium; William A. Cilley, Miami Valley Laboratories, P. O. Box 398707, Cincinnati, Ohio 45239-8707; Ronald A. Masters; Daniel W. Michael, both of Sharon Woods Technical Center, 11520 Reed Hartman Hwy., Cincinnati, Ohio 45141-2422; Eddy Vos, European Technical Center, Temselaan 100, B 1853 Strombeek-Bever, Belgium

[21] Appl. No.: 468,503

[22] Filed: Jun. 6, 1995

Related U.S. Application Data

[63] Continuation of Ser. No. 140,377, Oct. 21, 1993, abandoned, which is a continuation-in-part of Ser. No. 35,122, Mar. 19, 1993, Pat. No. 5,384,063.

[51] Int. Cl.[6] .................................................... C07C 43/11

[52] U.S. Cl. .................................................... 568/622

[58] Field of Search .................................................... 568/622

[56] References Cited

U.S. PATENT DOCUMENTS

| | | | |
|---|---|---|---|
| 2,508,035 | 5/1950 | Kosmin | 568/622 |
| 2,623,875 | 12/1952 | Schlossn et al. | 568/622 |
| 3,935,130 | 1/1976 | Hirano et al. | 252/542 |
| 3,962,149 | 6/1976 | Chirash et al. | 252/540 |
| 3,993,575 | 11/1976 | Howanitz | 252/142 |
| 4,247,408 | 1/1981 | Imamura et al. | 252/143 |
| 4,501,680 | 2/1985 | Aszman et al. | 252/142 |
| 4,581,161 | 4/1986 | Nedonchelle | 252/550 |
| 4,612,135 | 9/1986 | Wenzel | 252/106 |
| 4,759,865 | 7/1988 | Malihi | 252/175 |
| 4,886,917 | 12/1985 | Knopf et al. | 568/122 |
| 5,008,030 | 4/1991 | Cook et al. | 252/106 |
| 5,061,393 | 10/1991 | Linares et al. | 252/143 |
| 5,075,026 | 12/1991 | Loth et al. | 252/122 |

FOREIGN PATENT DOCUMENTS

| | | | |
|---|---|---|---|
| 894543 | 3/1983 | Belgium . | |
| 0125854A2 | 11/1984 | European Pat. Off. | C11D 1/83 |
| 0162600A1 | 11/1985 | European Pat. Off. | C11D 1/88 |
| 0496188A1 | 7/1992 | European Pat. Off. | C11D 3/20 |
| 62235399 | 10/1987 | Japan | C11D 1/72 |
| 1399966 | 7/1975 | United Kingdom | 568/622 |
| 1462133 | 1/1977 | United Kingdom | 568/622 |

*Primary Examiner*—Johann Richter
*Assistant Examiner*—John Peabody

[57] ABSTRACT

Detergent compositions comprising a surfactant system that is either (1) a mixture nonionic and zwitterionic detergent surfactants; (2) a mixture of nonionic and amphoteric (non-zwitterionic) detergent surfactants; or (3) short chain non-ionic detergent surfactant, the nonionic detergent surfactants preferably being short chain and/or having peaked distribution; optional hydrophobic cleaning solvent; and polycarboxylate, especially dicarboxylate, detergent builder provide superior cleaning of all of the soils commonly found in the bathroom. The compositions have a pH of from about 1 to about 5.5, preferably from about 2 to about 4 when the dicarboxylate builder is used. The compositions are in the form of aqueous liquids. Short chain peaked distribution nonionic detergent surfactants provide surprisingly superior sudsing characteristics.

2 Claims, No Drawings

ACIDIC LIQUID DETERGENT COMPOSITIONS FOR BATHROOMS

CROSS-REFERENCE TO RELATED APPLICATION

This is a continuation of application Ser. No. 08/140,377, filed on Oct. 21, 1993, now abandoned; which is a continuation-in-part of application Ser. No. 08/035,122, filed Mar. 19, 1993, now U.S. Pat. No. 5,384,063.

FIELD OF THE INVENTION

This invention pertains to acidic liquid detergent compositions for bathrooms. Such compositions typically contain detergent surfactants, detergent builders, and/or solvents to accomplish their cleaning tasks.

BACKGROUND OF THE INVENTION

The use of acidic cleaning compositions containing organic water-soluble synthetic detergents, solvents, and/or detergent builders for bathroom cleaning tasks are known. However, such compositions are not usually capable of providing superior hard surface cleaning for all of the soils encountered in a bathroom. An exception is the compositions of U.S. Pat. No. 5,061,393, Linares and Cilley, issued Oct. 29, 1991, said patent being incorporated herein by reference. The object of the present invention is to provide additional detergent compositions which also provide good and/or improved cleaning for all of the usual hard surface cleaning tasks found in the bathroom, including the removal of hard-to-remove soap scum and hard water deposits, and improved sudsing characteristics.

SUMMARY OF THE INVENTION

The present disclosure relates to an aqueous, acidic hard surface detergent composition comprising: (a) a detergent surfactant system which comprises either: (1) a mixture of nonionic and zwitterionic detergent surfactants as disclosed in U.S. Pat. No. 5,061,393, preferably a fatty acyl amidoalkylenebetaine; (2) a mixture of amphoteric (non-zwitterionic), preferably N-($C_{8-14}$ acylamidoalkylene) amidoglycinate, and nonionic detergent surfactants; or, less desirably, (3) a low sudsing, nonionic detergent surfactant that is a $C_{6-10}E_{3-12}$, preferably $C_{8-10}E_{3-8}$, nonionic detergent surfactant at a level of at least about 0.1%, preferably from about 1% to about 5%, the nonionic detergent surfactant in (1) and (2) preferably being one that has a short chain, e.g., $C_6$–$C_{10}$ $E_{3-12}$, more preferably being either a $C_8$ or mixture of $C_8$ and $C_{10}$ alkyl nonionic detergent surfactants with the $C_8$ being at least about 0.1% of the mixture, said low sudsing nonionic detergent surfactant optionally being a mixture of high HLB and low HLB nonionic detergent surfactants, and, also optionally, but preferably, all of the above surfactant combinations comprise short chain nonionic detergent surfactant having a "peaked distribution", i.e., at least about 70% of the molecules have a content of ethoxy moieties within about two of the average; (b) optionally, but preferably, hydrophobic solvent that provides a primary cleaning function, preferably butoxypropoxypropanol, and/or, e.g., the other solvents described in U.S. Pat. No. 5,061,393; and (c) poly-carboxylate detergent builder, preferably a dicarboxylic acid, having two carboxyl groups separated by from about 1 to about 4 carbon atoms, preferably as methylene groups, with said polycarboxylate detergent builder preferably containing at least about 2%, preferably from about 2% to about 14%, by weight of the composition, of said dicarboxylic acid, especially when detergent surfactant system (1) is present, and said composition having a pH of from about 1 to about 5.5, preferably from about 2 to about 4 when said dicarboxylic acid detergent builder is present.

The compositions can also contain an optional buffering system to help maintain the acidic pH and the balance typically being an aqueous solvent system and minor ingredients. The compositions can be formulated either as concentrates, or at usage concentrations, either thickened or unthickened, or can be packaged in a container having means for creating a spray or foam to make application to hard surfaces more convenient.

DETAILED DESCRIPTION OF THE INVENTION

(a) The Detergent Surfactant Systems

In accordance with the present invention, the detergent surfactant system is selected from the group consisting of: detergent surfactant systems which comprise either: (1) a mixture of nonionic and zwitterionic detergent surfactants as disclosed in U.S. Pat. No. 5,061,393, preferably a fatty acyl amidoalkylenebetaine; (2) a mixture of amphoteric (non-zwitterionic), preferably N-($C_{8-14}$ acylamidoalkylene)amidoglycinate, and nonionic detergent.surfactant; or, less desirably, (3) a low sudsing, nonionic detergent surfactant that is $C_{6-10}E_{3-12}$, preferably $C_{8-10}E_{3-8}$, nonionic detergent surfactant, the amount of ethoxylation being selected to give the appropriate HLB, at a level of at least about 0.1%, preferably from about 1% to about 5%, the nonionic detergent surfactant in (1) and (2) preferably being one that has a short chain, i.e., $C_{6-10}E_{3-12}$, more preferably being either a $C_8$ or mixture of $C_8$ and $C_{10}$ alkyl nonionic detergent surfactants with the $C_8$ being at least about 0.1% of the mixture, said low sudsing nonionic detergent surfactant optionally being a mixture of high HLB and low HLB nonionic detergent surfactants, and, optionally, but preferably, the nonionic detergent surfactant in all of the above surfactant combinations comprises short chain ($C_{6-10}$) nonionic detergent surfactant having a "peaked distribution", i.e, at least about 70% of the molecules have a content of ethoxy moieties within about two of the average, the content of said peaked short chain nonionic detergent surfactant preferably being at least about 0.1%. As mentioned hereinbefore, these shorter chain nonionic detergent surfactants, and especially those having a peaked distribution, are superior for use with the zwitterionic and/or amphoteric (non-zwitterionic) detergent surfactants.

The varied types of soils that may be encountered include oily/greasy soils and soap scum. The detergent surfactant systems of this invention provide good performance for all of the common types of soil encountered in the bathroom while providing superior sudsing characteristics. Specifically, the peaked distribution short chain nonionic detergent surfactants provide superior quantities of foam which quickly breaks to provide good rinsing. The short chain nonionic detergent surfactants are surprisingly effective when used with the betaine, especially amido-betaine type of zwitterionic detergent surfactant.

Amphoteric (Zwitterionic) Detergent Surfactants

Zwitterionic detergent surfactants contain both cationic and anionic hydrophilic groups on the same molecule at a relatively wide range of pH's. The typical cationic group is a quaternary ammonium group, although other positively charged groups like sulfonium and phosphonium groups can also be used. The typical anionic hydrophilic groups are carboxylates and sulfonates, although other groups like sulfates, phosphates, etc., can be used. A generic formula for some preferred zwitterionic detergent surfactants is:

$$R—N^{(+)}(R^2)(R^3)R^4X^{(-)}$$

wherein R is a hydrophobic group; $R^2$ and $R^3$ are each $C_{-4}$ alkyl, hydroxy alkyl or other substituted alkyl group which can also be joined to form ring structures with the N; $R^4$ is a moiety joining the cationic nitrogen atom to the hydrophilic group and is typically an alkylene, hydroxy alkylene, or polyalkoxy group containing from about one to about four carbon atoms; and X is the hydrophilic group which is preferably a carboxylate or sulfonate group.

Preferred hydrophobic groups R are alkyl groups containing from about 8 to about 22, preferably less than about 18, more preferably less than about 16, carbon atoms. The hydrophobic group can contain unsaturation and/or substituents and/or linking groups such as aryl groups, amido groups, ester groups, etc. In general, the simple alkyl groups are preferred for cost and stability reasons.

A specific "simple" zwitterionic detergent surfactant is 3-(N-dodecyl-N,N-dimethyl)-2-hydroxy-propane-1-sulfonate, available from the Sherex Company under the trade name "Varion HC."

Other specific zwitterionic detergent surfactants have the generic formula:

$$R—C(O)—N(R^2)—(CR^3{}_2)_n—N(R^2)_2{}^{(+)}—(CR^3{}_2)_n—SO_2{}^{(-)}$$

wherein each R is a hydrocarbon, e.g., an alkyl group containing from about 8 up to about 20, preferably up to about 18, more preferably up to about 16 carbon atoms, each ($R^2$) is either a hydrogen (when attached to the amido nitrogen), short chain alkyl or substituted alkyl containing from one to about four carbon atoms, preferably groups selected from the group consisting of methyl, ethyl, propyl, hydroxy substituted ethyl or propyl and mixtures thereof, preferably methyl, each ($R^3$) is selected from the group consisting of hydrogen and hydroxy groups, and each n is a number from 1 to about 4, preferably from 2 to about 3; more preferably about 3, with no more than about one hydroxy group in any ($CR^3{}_2$) moiety. The R groups can be branched and/or unsaturated, and such structures can provide spotting/filming benefits, even when used as part of a mixture with straight chain alkyl R groups. The $R^2$ groups can also be connected to form ring structures. A detergent surfactant of this type is a $C_{10-14}$ fatty acylamidopropylene(hydroxypropylene)sulfobetaine that is available from the Sherex Company under the trade name "Varion CAS Sulfobetaine".

Compositions of this invention containing the above hydrocarbyl amido sulfobetaine (HASB) can contain more perfume and/or more hydrophobic perfumes than similar compositions containing conventional anionic detergent surfactants. This can be desirable in the preparation of consumer products. Perfumes useful in the compositions of this invention are disclosed in more detail hereinafter.

Other zwitterionic detergent surfactants useful, and, surprisingly, preferred, herein include hydrocarbyl, e.g., fatty, amidoalkylenebetaines (hereinafter also referred to as "HAB"). These detergent surfactants, which are more cationic at the pH of the composition, have the generic formula:

$$R—C(O)—N(R^2)—(CR^3{}_2)_n—N(R^2)_2{}^{(+)}—(CR^3{}_2)_n—C(O)O^{(-)}$$

wherein each R is a hydrocarbon, e.g., an alkyl group containing from about 8 up to about 20, preferably up to about 18, more preferably up to about 16 carbon atoms, each ($R^2$) is either a hydrogen (when attached to the amido nitrogen), short chain alkyl or substituted alkyl containing from one to about four carbon atoms, preferably groups selected from the group consisting of methyl, ethyl, propyl, hydroxy substituted ethyl or propyl and mixtures thereof, preferably methyl, each ($R^3$) is selected from the group consisting of hydrogen and hydroxy groups, and each n is a number from 1 to about 4, preferably from 2 to about 3; more preferably about 3, with no more than about one hydroxy group in any ($CR^3{}_2$) moiety. The R groups can be branched and/or unsaturated, and such structures can provide spotting/filming benefits, even when used as part of a mixture with straight chain alkyl R groups.

An example of such a detergent surfactant is a $C_{10-14}$ fatty acylamidopropylenebetaine available from the Miranol Company under the trade name "Mirataine CB."

The level of zwitterionic detergent surfactant, when present in the composition, is typically from about 0.01% to about 8%, preferably from about 1% to about 6%, more preferably from about 2% to about 4%. The level in the composition is dependent on the eventual level of dilution to make the wash solution. For cleaning, the composition, when used full strength, or the wash solution containing the composition, should contain from about 0.01% to about 8%, preferably from about 1% to about 6%, more preferably from about 2% to about 4%, of the zwitterionic detergent surfactant. Concentrated products will typically contain from about 0.02% to about 16%, preferably from about 4% to about 8% of the zwitterionic detergent surfactant.

Nonionic Detergent Surfactant or Cosurfactant

Compositions of this invention contain nonionic detergent surfactant, either alone, or as part of a mixture with a zwitterionic, or amphoteric, detergent surfactant ("cosurfactant") to provide cleaning and emulsifying benefits over a wide range of soils. Nonionic detergent surfactants useful herein include any of the well-known nonionic detergent surfactants that have an HLB of from about 6 to about 18, preferably from about 8 to about 16, more preferably from about 8 to about 10. Mixtures of high and low HLB nonionic detergent surfactants can also be used. High HLB nonionic detergent surfactants have an HLB above about 12, preferably above about 14, and more preferably above about 15, and low HLB nonionic detergent surfactants have an HLB of below about 10, preferably below about 9, and more preferably below about 8.5. The difference between the high and low HLB values should preferably be at least about 4.

The nonionic detergent surfactant preferably should comprise the peaked nonionic detergent surfactants mentioned hereinbefore. A "peaked" nonionic detergent surfactant is preferably one in which at least about 70%, more preferably at least about 80%, more preferably about 90%, of the molecules, by weight, contain within two ethoxy groups (moieties) of the average number of ethoxy groups. Peaked nonionic detergent surfactants have superior odor as compared to nonionic detergent surfactants having a "normal" distribution in which only about 60% of the molecules contain within two ethoxy groups of the average number of ethoxy groups.

Also, surprisingly, the short chain ($C_{6-10}$) nonionic detergent surfactants, and especially the peaked short chain nonionic detergent surfactants, when combined with amphoteric and/or zwitterionic detergent surfactants, especially those that contain a carboxy group, in the acidic compositions, provide superior sudsing properties. The suds (foam) is superior both in quantity and in the speed with which the suds break as compared to similar combinations with conventional nonionic detergent surfactants and the peaked surfactants are better than similar short chain nonionic detergent surfactants having a normal distribution. The HLB of the peaked short chain nonionic detergent surfactants is typically from about 6 to about 18, preferably from about 8 to about 16, more preferably from about 8 to about 10, and, as before, mixed low and high HLB short chain peaked nonionic detergent surfactants should differ in HLB by at least about 4. In the typical "peaked" distribution at least about 70%, preferably at least about 80%, and more preferably at least about 90%, but less than about 95%, of the nonionic detergent surfactant contains a number of ethoxy moieties within two of the average number of ethoxy moieties.

One preferred nonionic detergent surfactant is either an octyl polyethoxylate, or mixtures of octyl and decyl polyethoxylates with from about 0.1% to about 15%, preferably from about 1% to about 5%, of said octyl polyethoxylate. Another preferred polyethoxytate is a mixture of $C_6$, $C_8$, and $C_{10}$ polyethoxylates containing from about 40% to about 80%, preferably from about 50% to about 70%, by weight ethoxy moieties in a peaked distribution. This latter polyethoxylate is especially desirable when the composition is to be used both at full strength and with dilution.

Typical of the more conventional nonionic detergent surfactants useful herein are alkoxylated (especially ethoxylated) alcohols and alkyl phenols, and the like, which are well known from the detergency art. In general, such nonionic detergent surfactants contain an alkyl group in the $C_{6-22}$, preferably $C_{6-10}$, more preferably all $C_8$ or mixtures of $C_{8-10}$, as discussed hereinbefore, and generally contain from about 2.5 to about 12, preferably from about 4 to about 10, more preferably from about 5 to about 8, ethylene oxide groups, to give an HLB of from about 8 to about 16, preferably from about 10 to about 14. Ethoxylated alcohols are especially preferred in the compositions of the present type.

Specific examples of nonionic detergent surfactants useful herein include: octyl polyethoxylates (2.5) and (5); decyl polyethoxylates (2.5) and (5); decyl polyethoxylate (6); mixtures of said octyl and decyl polyethoxylates with at least about 10%, preferably at least about 30%, more preferably at least about 50%, of said octyl polyethoxylate; and coconut alkyl polyethoxylate (6.5). Peaked cut nonionic detergent surfactants include a $C_{8-10}E_5$ in which the approximate distribution of ethoxy groups, by weight, is 0=1.2; 1=0.9; 2=2.4; 3=6.3; 4=14.9; 5=20.9; 6=21.5; 7=16.4; 8=9.4; 9=4.1; 10=1.5; 11=0.5; and 12=0.1 and a $C_{8-10}E_7$ in which the approximate distribution of ethoxy groups, by weight, is 0=0.2; 1=0.2; 2=0.5; 3=1.5; 4=6.0; 5=10.2; 6=17.2; 7=20.9; 8=18.9; 9=13.0; 10=7.0; 11=3.0; 12=1.0; 13=0,3; and 14=0.1

Short chain nonionic detergent surfactant having a peaked distribution in which at least about 70% and less than about 95% of the molecules by weight have an ethoxy content within about two ethoxy moieties of the average ethoxy content can be used. The short chain nonionic detergent surfactant can be a $C_{6-11}E_{3-12}$ which has a peaked distribution in which at least about 80% of the molecules by weight have an ethoxy content within about two ethoxy moieties of the average ethoxy content.

A detailed listing of suitable nonionic surfactants, of the above types, for the detergent compositions herein can be found in U.S. Pat. No. 4,557,853, Collins, issued Dec. 10, 1985, incorporated by reference herein. Commercial sources of such surfactants can be found in McCutcheon's EMULSIFIERS AND DETERGENTS, North American Edition, 1984, McCutcheon Division, MC Publishing Company, also incorporated herein by reference.

The nonionic surfactant component can comprise as little as 0.01% of the compositions herein, especially when used with another detergent surfactant, but typically the compositions will contain from about 0.5% to about 6%, more preferably from about 1% to about 4%, of nonionic cosurfactant, and when the short chain $C_8$ or $C_{8-10}$ polyethoxylate detergent surfactant is used alone, the amount is from about 0.1% to about 15%, preferably from about 1% to about 8%, more prefrerably from about 2% to about 6%.

The ratio of nonionic surfactant to zwitterionic or amphoteric (non-zwitterionic) detergent surfactant is typically from about 1:4 to about 3:1, preferably from about 1:3 to about 2:1, more preferably from about 1:2 to about 1:1.

Amphoteric (Non-zwitterionic) Detergent Surfactant

These detergent surfactants are similar to the zwitterionic detergent surfactants, but without the quaternary group. However, they contain an amine group that is protonated at the low pH of the composition (below pH 5.5), to form a cationic group, and they may also possess an anionic group at these pHs.

One suitable amphoteric detergent surfactant is a $C_{8-14}$ amidoalkylene glycinate detergent surfactant. These detergent surfactants are essentially cationic at the acid pH.

The glycinate detergent surfactants herein preferably have the generic formula, as an acid, of:

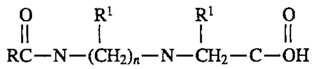

wherein

is a $C_{8-14}$, preferably $C_{8-10}$, hydrophobic fatty acyl moiety containing from about 8 to about 14, preferably from about 8 to about 10, carbon atoms which, in combination with the nitrogen atom, forms an amido group, each n is from 1 to 3, and each $R^1$ is hydrogen (preferably) or a $C_{1-2}$ alkyl or hydroxy alkyl group. Such detergent surfactants are available, e.g., in the salt form, for example, from Sherex under the trade name Rewoteric AM-V, having the formula:

$$C_7C(O)NH(CH_2)_2N(CH_2CH_2OH)CH_2C(O)O^{(-)}\ Na^{(+)}.$$

Not all amphoteric detergent surfactants are acceptable. Longer chain glycinates and similar substituted amino propionates provide a much lower level of cleaning. Such propionates are available as, e.g., salts from Mona Industries, under the trade name Monateric 1000, having the formula:

$C_7C(O)NH(CH_2)_2N(CH_2CH_2OH)CH_2CH_2C(O)O^{(-)}\ Na^{(+)}$.

Cocoyl amido ethyleneamine-N-(hydroxyethyl)-2-hydroxypropyl-1-sulfonate (Miranol CS); $C_{8-10}$ fatty acyl amidoethyleneamine-N-(methyl)ethyl sulfonate; and analogs and homologs thereof, as their water-soluble salts, or acids, are amphoterics that provide good cleaning. Preferably, these amphoterics are combined with the short chain nonionic detergent surfactants to minimize sudsing.

Examples of other suitable amphoteric (non-zwitterionic) detergent surfactants include:

cocoylamido ethyleneamine-N-(methyl)-acetates;

cocoylamido ethyleneamine-N-(hydroxyethyl)-acetates;

cocoylamido propyl amine-N-(hydroxyethyl)-acetates; and analogs and homologs thereof, as their water-soluble salts, or acids, are suitable.

Optional Anionic Detergent Surfactant

Typical optional anionic detergent surfactants are the alkyl- and alkyl(polyethoxylate) sulfates, paraffin sulfonates, olefin sulfonates, alpha-sulfonates of fatty acids and of fatty acid esters, and the like, which are well known from the detergency art. In general, such detergent surfactants contain an alkyl group in the $C_{9-22}$ preferably $C_{10-18}$, more preferably $C_{12-16}$, range. The anionic detergent surfactants can be used in the form of their sodium, potassium or alkanolammonium, e.g., triethanolammonium salts. $C_{12-18}$ paraffin-sulfonates and alkyl sulfates are especially preferred in the compositions of the present type.

A detailed listing of suitable anionic detergent surfactants, of the above types, for the detergent compositions herein can be found in U.S. Pat. No. 4,557,853, Collins, issued Dec. 10, 1985, incorporated by reference hereinbefore. Commercial sources of such surfactants can be found in McCutcheon's EMULSIFIERS AND DETERGENTS, North American Edition, 1984, McCutcheon Division, MC Publishing Company, also incorporated hereinbefore by reference.

The optional anionic detergent cosurfactant component can comprise as little as 0.001% of the compositions herein when it is present, but typically the compositions will contain from about 0.01% to about 5%, more preferably from about 0.02% to about 2%, of anionic detergent cosurfactant, when it is present. Anionic detergent surfactants are desirably not present, or are present only in limited amounts to promote rinsing of the surfaces.

(b) The Optional Hydrophobic Solvent

In order to obtain the best cleaning, especially of lipid soils, it is necessary to use a hydrophobic solvent that has cleaning activity. The solvents employed in the hard surface cleaning compositions herein can be any of the well-known "degreasing" solvents commonly used in, for example, the dry cleaning industry, in the hard surface cleaner industry and the metalworking industry. The level of hydrophobic solvent is preferably, and typically, from about 1% to about 15%, preferably from about 2% to about 12%, most preferably from about 5% to about 10%.

Many of such solvents comprise hydrocarbon or halogenated hydrocarbon moieties of the alkyl or cycloalkyl type, and have a boiling point well above room temperature, i.e., above about 20° C.

The formulator of compositions of the present type will be guided in the selection of solvent partly by the need to provide good grease-cutting properties, and partly by aesthetic considerations.

Generically, the glycol ethers useful herein have the formula $R^1$-O-($R^2$O)-H wherein each $R^1$ is an alkyl group which contains from about 4 to about 8 carbon atoms, each $R^2$ is either ethylene or propylene, and m is a number from 1 to about 3, and the compound has a solubility in water of less than about 20%, preferably less than about 10%, and more preferably less than about 6%. The most preferred glycol ethers are selected from the group consisting of dipropyleneglycolmonobutyl ether, monopropyleneglycolmonobutyl ether, diethyleneglycolmonohexyl ether, monoethyleneglycolmonohexyl ether, monoethylene glycolmonobutyl ether, and mixtures thereof.

The monopropyleneglycolmonobutyl ether (butoxy-propanol) solvent should have no more than about 20%, preferably no more than about 10%, more preferably no more than about 7%, of the secondary isomer in which the butoxy group is attached to the secondary atom of the propanol for improved odor.

Solvents for these hard surface cleaner compositions can also comprise diols having from 6 to about 16 carbon atoms in their molecular structure. Preferred diol solvents have a solubility in water of from about 0.1 to about 20 g/100 g of water at 20° C. The diol solvents in addition to good grease cutting ability, impart to the compositions an enhanced ability to remove calcium soap soils from surfaces such as bathtub and shower stall walls. These soils are particularly difficult to remove, especially for compositions which do not contain an abrasive.

Other solvents such as benzyl alcohol, n-hexanol, and phthalic acid esters of $C_{1-4}$ alcohols can also be used.

Terpene solvents and pine oil, are usable, but are preferably not present.

(c) The Polycarboxylate Detergent Builder

Polycarboxylate detergent builders useful herein, include the builders disclosed in U.S. Pat. No. 4,915,854, Mao et al., issued Apr. 10, 1990, said patent being incorporated herein by reference. Suitable detergent builders preferably have relatively strong binding constants for calcium under acid conditions.

Preferred detergent builders include dicarboxylic acids having from about 2 to about 14, preferably from about 2 to about 4, carbon atoms between the carboxyl groups. Specific dicarboxylic detergent builders include succinic, glutaric, and adipic acids, and mixtures thereof. Such acids have a $pK_1$ of more than about 3 and have relatively high calcium salt solubilities. Substituted acids having similar properties can also be used.

These dicarboxylic detergent builders provide faster removal of the hard water soils, especially when the pH is between about 2 and about 4.

Other suitable builders that can be used include: citric acid, and, especially, builders having the generic formula:

$$R^5\text{-}[O\text{—}CH(COOH)CH(COOH)]_nR^5$$

wherein each $R^5$ is selected from the group consisting of H and OH and n is a number from about 2 to about 3 on the average. Other preferred detergent builders include those described in the U.S. Pat. No. 5,051,212, Culshaw and Vos, issued Sep. 24, 1991, for "Hard-Surface Cleaning Compositions," said patent being incorporated herein by reference.

In addition to the above detergent builders, other detergent builders that are relatively efficient for hard surface cleaners and/or, preferably, have relatively reduced filming/streaking characteristics include the acid forms of those disclosed in U.S. Pat. No. 4,769,172, Siklosi, issued Sep. 6, 1988, and incorporated herein by reference. Still others include the chelating agents having the formula:

$$R\text{-}N\ (CH_2COOM)_2$$

wherein R is selected from the group consisting of: $—CH_2CH_2CH_2OH$; $—CH_2CH(OH)CH_2$; $—CH_2CH(OH)CH_2OH$; $—CH(CH_2OH)_2$; $—CH_3$; $—CH_2CH_2OCH_3$;

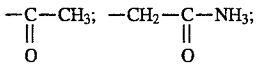

$—CH_2CH_2CH_2OCH_3$; $—C(CH_2OH)_3$; and mixtures thereof; and each M is hydrogen.

The chelating agents of the invention are present at levels of from about 2% to about 14% of the total composition, preferably about 3% to about 12%, more preferably from about 5% to about 10%.

The acidic detergent builders herein will normally provide the desired pH in use. However, if necessary, the composition can also contain additional buffering materials to give a pH in use of from about 1 to about 5.5, preferably from about 2 to about 4.5, more preferably from about 2 to about 4. pH is usually measured on the product. The buffer is selected from the group consisting of: mineral acids such as HCl, $HNO_3$, etc. and organic acids such as acetic, etc., and mixtures thereof. The buffering material in the system is important for spotting/filming. Preferably, the compositions are substantially, or completely free of materials like oxalic acid that are typically used to provide cleaning, but which are not desirable from a safety standpoint in compositions that are to be used in the home, especially when very young children are present.

The Aqueous Solvent System

The balance of the formula is typically water. Nonaqueous polar solvents with only minimal cleaning action like methanol, ethanol, isopropanol, ethylene glycol, propylene glycol, and mixtures thereof are usually not present. When the nonaqueous solvent is present, the level of nonaqueous polar solvent is from about 0.5% to about 10%, preferably less than about 5% and the level of water is from about 50% to about 97%, preferably from about 75% to about 95%.

Optional Ingredients

The compositions herein can also contain other various adjuncts which are known to the art for detergent compositions so long as they are not used at levels that cause unacceptable spotting/filming. Nonlimiting examples of such adjuncts are:

Enzymes such as proteases;

Hydrotropes such as sodium toluene sulfonate, sodium cumene sulfonate and potassium xylene sulfonate; and Aesthetic-enhancing ingredients such as colorants and perfumes, providing they do not adversely impact on spotting/filming in the cleaning of glass. The perfumes are preferably those that are more water-soluble and/or volatile to minimize spotting and filming.

Hydrotropes

Hydrotropes are highly preferred optional ingredients. In addition to providing the normal benefits associated with hydrotropes, e.g., phase stability and/or viscosity reduction, hydrotropes can also provide improved suds characteristics. Specifically, when the zwitterionic and/or amphoteric detergent surfactants contain a carboxy group as the anionic group, the hydrotrope can improve both the quantity of suds generated, especially when the product is dispensed from a sprayer or foamer, and, at the same time, reduce the amount of time required for the foam to "break", i.e., the time until the foam has disappeared. Both of these characteristics are valued by consumers, but they are usually considered to be mutually incompatible. The hydrotropes that provide the optimum suds improvements are anionic, especially the benzene and/or alkyl benzene sulfonates. The usual examples of such hydrotropes are the benzene, toluene, xylene, and cumene sulfonates. Typically, these hydrotopes are available as their salts, most commonly the sodium salts. Preferably, the hydrotrope is present in at least about molar equivalency to the zwitterionic and/or amphoteric detergent surfactants. Typical levels of hydrotropes are from about 0.1% to about 5%, preferably from about 1% to about 3%.

Perfumes

Most hard surface cleaner products contain some perfume to provide an olfactory aesthetic benefit and to cover any "chemical" odor that the product may have. The main function of a small fraction of the highly volatile, low boiling (having low boiling points), perfume components in these perfumes is to improve the fragrance odor of the product itself, rather than impacting on the-subsequent odor of the surface being cleaned. However, some of the less volatile, high boiling perfume ingredients can provide a fresh and clean impression to the surfaces, and it is sometimes desirable that these ingredients be deposited and present on the dry surface. Perfume ingredients are readily solubilized in the compositions by the nonionic and zwitterionic detergent surfactants. Anionic detergent surfactants will not solubilize as much perfume, especially substantive perfume, or maintain uniformity to the same low temperature.

The perfume ingredients and compositions of this invention are the conventional ones known in the art. Selection of any perfume component, or amount of perfume, is based solely on aesthetic considerations. Suitable perfume compounds and compositions can be found in the art including U.S. Pat. No. : 4,145,184, Brain and Cummins, issued Mar. 20, 1979; U.S. Pat. No. 4,209,417, Whyte, issued Jun 24, 1980; U.S. Pat. No. 4,515,705, Moeddel, issued May 7, 1985; and U.S. Pat. No. 4,152,272, Young, issued May 1, 1979, all of said patents being incorporated herein by reference.

In general, the degree of substantivity of a perfume is roughly proportional to the percentages of substantive perfume material used. Relatively substantive perfumes contain at least about 1%, preferably at least about 10%, substantive perfume materials.

Substantive perfume materials are those odorous compounds that deposit on surfaces via the cleaning process and are detectable by people with normal olfactory acuity. Such materials typically have vapor pressures lower than that of the average perfume material. Also, they typically have molecular weights of about 200 or above, and are detectable at levels below those of the average perfume material.

Perfume ingredients useful herein, along with their odor character, and their physical and chemical properties, such as boiling point and molecular weight, are given in "Perfume and Flavor Chemicals (Aroma Chemicals)," Steffen Arctander, published by the author, 1969, incorporated herein by reference.

Examples of the highly volatile, low boiling, perfume ingredients are: anethole, benzaldehyde, benzyl acetate, benzyl alcohol, benzyl formate, isobornyl acetate, camphene, cis-citral (neral), citronellal, citronellol, citronellyl acetate, paracymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95% of d-limonene.

Examples of moderately volatile perfume ingredients are: amyl cinnamic aidehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aidehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

Examples of the less volatile, high boiling, perfume ingredients are: benzophenone, benzyl salicylate, ethylene brassylate, galaxolide (1,3,4,6,7,8-hexahydro-4,6,6,7,8,8-hexamethylcyclo-penta-gamma-2-benzopyran), hexyl cinnamic aidehyde, lyral (4-(4-hydroxy-4-methyl pentyl)-3-cyclohexene-10-carboxaldehyde), methyl cedrylone, methyl dihydro jasmonate, methyl-beta-naphthyl ketone, musk indanone, musk ketone, musk tibetene, and phenylethyl phenyl acetate.

Selection of any particular perfume ingredient is primarily dictated by aesthetic considerations, but more water-soluble materials are preferred, as stated hereinbefore, since such materials are less likely to adversely affect the good spotting/filming properties-of the compositions.

These compositions have exceptionally good cleaning properties. They also have good "shine" properties, i.e., when used to clean glossy surfaces, without rinsing, they have much less tendency than e.g., phosphate built products to leave a dull finish on the surface.

In a preferred process for using the products described herein, and especially those formulated to be used at full strength, the product is sprayed onto the surface to be cleaned and then wiped off with a suitable material like cloth, a paper towel, etc. It is therefore highly desirable to package the product in a package that comprises a means for creating a spray, e.g., a pump, aerosol propellant and spray valve, etc.

All parts, percentages, and ratios herein are "by weight" unless otherwise stated.

The invention is illustrated by the following Examples.

EXAMPLE I

| Ingredient | Wt. % |
|---|---|
| 3-(N-dodecyl-N,N-dimethyl)-2-hydroxy-propane-1-sulfonate (DDHPS)[1] | 2.0 |
| Octyl polyethoxylate(2.5) (OPE2.5) | 1.1 |
| Octyl polyethoxylate(6.0) (OPE6) | 2.9 |
| Butoxy Propoxy Propanol (BPP) | 5.0 |
| Succinic Acid | 10.0 |
| Sodium Cumene Sulfonate (SCS) | 4.2 |
| Water, Buffering Agents, and Minors | up to 100 |
| pH | 3.0 |

[1]Varion CAS

EXAMPLE II

| Ingredient | Wt. % |
|---|---|
| N-(Coconutamidoethylene)-N-(hydroxyethyl)-glycine[1] | 2.0 |
| $C_{9-11}$ Polyethoxylate (6) (C91E6)[2] | 2.0 |
| BPP | 8.0 |
| Citric Acid | 10.0 |
| SCS | 1.6 |
| Water, Buffering Agents, and Minors | up to 100 |
| pH | 2.97 |

[1]Rewoteric AM-V
[2]Neodol 91-6

EXAMPLE III

| Ingredient | A Wt. % | B Wt. % | C Wt. % |
|---|---|---|---|
| 3-(N-dodecyl-N,N-dimethyl)-2-hydroxy-propane-1-sulfonate (DDHPS)[1] | 2.0 | — | — |
| $C_{9-11}$ Polyethoxylate (6) (C91E6)[2] | 2.0 | — | — |
| $C_{8-10}$ E6 | — | 2.0 | 2.0 |
| Cocoamido propyl betaine[3] | — | 2.0 | — |
| N-(Coconutamidoethylene)-N-(hydroxyethyl)-glycine[4] | — | — | 2.0 |
| BPP | 8.0 | 8.0 | 8.0 |
| Citric Acid | 6.0 | 6.0 | 6.0 |
| SCS | 1.6 | 1.6 | 1.6 |
| Water, Buffering Agents, and Minors | | up to 100 | |
| pH | 2.97 | 2.97 | 12.97 |

[1]Varion CAS
[2]Neodol 91-6
[3]Betaine AMB-15
[4]Rewoteric AM-V

The above compositions are tested for cleaning using a moderate/heavy soap scum on tile. The test is run as follows:

Standard soiled tiles that are used to provide a reproducible, standard soiled surface are treated with each product and five seconds later the surface is rubbed twice with a Gardner Straight-line Washability Machine. All treatments are full product and all treatments are the same. Three expert judges grade the tiles using a scale in which 0=no visible soil and 8="extreme soil".

The grades on the 0–8 scale are: A–2.1; B–1.2, and C–2.7 with an $LSD_{05}$ of about 0.7. B, especially, gives good results. The improved performance of B is totally unexpected and it is surprising that an amphoteric like the glycinate that is essentially cationic at pH 5.5 is satisfactory.

EXAMPLE IV

| Ingredient | A Wt. % | B Wt. % | C Wt. % | D Wt. % |
|---|---|---|---|---|
| 3-(N-dodecyl-N,N-dimethyl)-2-hydroxy-propane-1-sulfonate (DDHPS)[1] | 2.0 | 2.0 | 2.0 | 2.0 |
| $C_{9-11}$ Polyethoxylate (6) (C91E6)[2] | 2.0 | — | — | — |
| $C_{10}E6$[3] | — | 2.0 | — | — |
| $C_8E6$[4] | — | — | 2.0 | — |
| $C_6E6$[5] | — | — | — | 2.0 |
| BPP | 8.0 | 8.0 | 8.0 | 8.0 |
| Citric Acid | 6.0 | 6.0 | 6.0 | 6.0 |
| SCS | 1.6 | 1.6 | 1.6 | 1.6 |
| Water, Buffering Agents, and Minors | | up to 100 | | |
| pH | 2.97 | 2.98 | 2.98 | 3.10 |

[1]Varion CAS
[2]Neodol 91-6
[3]Sulfonic L10-6
[4]Sulfonic L8-6
[5]Sulfonic L6-6

The above formulas are tested as in Example III with the results as follows ($LSD_{95}$ of 0.8): A–2.3; B–2.4; C–2.2; and D–4.4. It is surprising that the lower sudsing C formula is equal to A and/or B formulas.

EXAMPLE V

| Ingredient | A Wt. % | Glycinates<br>B Wt. % | C Wt. % |
|---|---|---|---|
| 3-(N-dodecyl-N,N-dimethyl)-2-hydroxy-propane-1-sulfonate (DDHPS)[1] | 2.0 | — | — |
| $C_{9-11}$ Polyethoxylate (6) (C91E6)[2] | 2.0 | 2.0 | 2.0 |
| $C_{8-10}$ E6 | — | 2.0 | 2.0 |
| Lauroamphoglycinate[3] | — | 2.0 | — |
| Tallow Glycinate[4] | — | — | 2.0 |
| BPP | 8.0 | 8.0 | 8.0 |
| Citric Acid | 6.0 | 6.0 | 6.0 |
| SCS | 3.0 | 3.0 | 3.0 |
| Water, Buffering Agents, and Minors | | up to 100 | |
| pH | 2.95 | 3.23 | 3.05 |

[1]Varion CAS
[2]Neodol 91-6
[3]Rewoteric AM 2L-35
[4]Rewoteric AM TEG

EXAMPLE V (Continued)

| Ingredient | Propionates<br>D Wt. % | E Wt. % |
|---|---|---|
| $C_{9-11}$ Polyethoxylate (6) (91E6)[1] | 2.0 | 2.0 |
| Cocamphopropionate[2] | 2.0 | — |
| Sodium Lauryliminodipropionate[3] | — | 2.0 |
| BPP | 8.0 | 8.0 |
| Citric Acid | 6.0 | 6.0 |
| SCS | 3.0 | 3.0 |
| Water, Buffering Agents, and Minors | up to 100 | |
| pH | 3.34 | 3.37 |

[1]Neodol 91-6
[2]Rewoteric AM 2CSF
[3]Rewoteric AM LP

EXAMPLE V (Continued)

| Ingredient | F Wt. % | Betaines<br>G Wt. % | H Wt. % |
|---|---|---|---|
| $C_{9-11}$ Polyethoxylate (6) (C91E6)[1] | 2.0 | 2.0 | 2.0 |
| $C_{8-10}$ E6 | — | 2.0 | 2.0 |
| Cocamido Propyl Betaine[2] | 2.0 | — | — |
| Coco Amidopropyl Betaine[3] | — | 2.0 | — |
| Lauryl Betaine[4] | — | — | 2.0 |
| BPP | 8.0 | 8.0 | 8.0 |
| Citric Acid | 6.0 | 6.0 | 6.0 |
| SCS | 3.0 | 3.0 | 3.0 |
| Water, Buffering Agents, and Minors | | up to 100 | |
| pH | 3.03 | 3.01 | 3.12 |

[1]Neodol 91-6
[2]Rewoteric AM B14-U
[3]Rewoteric AM B15-U
[4]Rewoteric DML-35

The formulas in V are tested as in III with the results as follows ($LSD_{95}$ at about 0.7): A–1.3; B –1.4; C–5.3; D–3.34; E–3.1; F–1.3; G–1.0; and H–1.8. Again, the betaines, especially, are surprisingly good and the glycinate amphoteric is much better than the adjacent propionate.

EXAMPLE VI

| Ingredient | A Wt. % | B Wt. % |
|---|---|---|
| 3-(N-dodecyl-N,N-dimethyl)-2-hydroxy-propane-1-sulfonate (DDHPS)[1] | 2.0 | 2.0 |
| $C_{9-11}$ Polyethoxylate (6) (C91E6)[2] | 2.0 | 2.0 |
| BPP | 8.0 | 8.0 |
| Citric Acid | 6.0 | — |
| Succinic Acid | — | 6.0 |
| SCS | 3.0 | 3.0 |
| Water, Buffering Agents, and Minors | up to 100 | |
| pH | 2.95 | 3.01 |

[1]Varion CAS
[2]Neodol 91-6

The above formulas are tested as in III and found equivalent, but when tested by exposing the wash solutions to marble chips, which are representative of hard water calcium carbonate deposits, B is indexed at 190 as compared to A's 100. Also, on lower grade colored enamels, B shows no discoloration, whereas A shows a slight discoloration.

EXAMPLE VII

| Ingredient | Comparative Example Wt. % | B Wt. % |
|---|---|---|
| 3-(N-dodecyl-N,N-dimethyl)-2-hydroxy-propane-1-sulfonate (DDHPS)[1] | 2.0 | — |
| Cocoylamido Propylene Betaine[2] | — | 2.0 |
| $C_{9-11}$ Polyethoxylate (6) (C91E6)[3] | 2.0 | 2.0 |
| BPP | 8.0 | 8.0 |
| Citric Acid | 6.0 | 6.0 |
| SCS | 3.0 | 3.0 |
| Water, Buffering Agents, and Minors | up to 100 | |
| pH | 2.95 | 3.01 |

[1]Varion CAS
[2]Betaine AMB-15-V
[3]Neodol 91-6

The above formulas are tested as in III. The soap scum grade for A is 1.9 and for B is 0.9 with an LSD at 95% of 0.6. The commercial product which is the market leader has a grade of 5.1. B is clearly superior to both A and the market leader.

EXAMPLE VIII

| Ingredient | A Wt. % | B Wt. % |
|---|---|---|
| $C_{8-10}$ E6 | 2.0 | 2.0 |
| Cocoamido propyl betaine[1] | 2.0 | 2.0 |
| BPP | 8.0 | 8.0 |
| Succinic Acid | 6.0 | 6.0 |
| SCS | 1.6 | 1.6 |
| Water, Buffering Agents, and Minors | up to 100 | |
| pH | 2.00 | 4.5 |

[1]Betaine AMB-15

EXAMPLE IX

| Ingredient | A Wt. % | B Wt. % | C Wt. % |
|---|---|---|---|
| 3-(N-dodecyl-N,N-dimethyl)-2-hydroxy-propane-1-sulfonate (DDHPS)[1] | 2.0 | — | — |
| Cocoylamidopropyl Betaine[2] | — | 1.75 | 1.75 |
| $C_{9-11}$ Polyethoxylate (6) (C91E6)[3] | 2.0 | — | — |
| $C_{8-10}$ Polyethoxylate (6) (peaked cut $C_{8-10}E_6$)[4] | — | 2.0 | 2.0 |
| BPP | 8.0 | 6.0 | 6.0 |
| Citric Acid | 6.0 | 6.0 | 6.0 |
| SCS | 3.0 | — | 2.0 |
| Water, Buffering Agents, and Minors | | up to 100 | |
| pH | 3.0 | 3.0 | 3.0 |

[1]Varion CAS
[2]Betaine AMB-15-V
[3]Neodol 91-6
[4]Peaked cut $C_{8-0}E_6$ as described hereinbefore.

The above formulas are sprayed through T-8900 sprayers available from Continental Sprayers, Inc. The C formula provides better performance with less total active materials than the comparative A. formula. In addition, the approximate volume of suds in cc of suds per cc of product for the A, B, and C, formulas is: A–3.6; B–4.0; and C–5 9 while the approximate time for the suds to "break" in seconds is: A–9.25; B–6.4; and C–4.0. As can be seen from this comparison, the effect of the hydrotrope, in addition to selection of the zwitterionic detergent surfactant containing the carboxy group, provides both more suds and suds which break quicker.

EXAMPLE X

| Ingredient | A Wt. % | B Wt. % | C Wt. % |
|---|---|---|---|
| 3-(N-dodecyl-N,N-dimethyl)-2-hydroxy-propane-1-sulfonate (DDHPS)[1] | 2.0 | — | — |
| Cocoylamidopropyl Betaine[2] | — | 1.75 | 1.75 |
| $C_{9-11}$ Polyethoxylate (6) (C91E6)[3] | 2.0 | — | — |
| $C_{8-10}$ Polyethoxylate (6) (peaked cut $C_{8-10}E_6$)[4] | — | 2.0 | 2.0 |
| BPP | 8.0 | 6.0 | 6.0 |
| Citric Acid | 6.0 | 6.0 | 6.0 |
| SCS | 3.0 | — | 2.0 |
| Xanthan Gum | 0.23 | 0.23 | 0.23 |
| Water, Buffering Agents, and Minors | | up to 100 | |
| pH | 3.0 | 3.0 | 3.0 |

[1]Varion CAS
[2]Betaine AMB-15-V
[3]Neodol 91-6
[4]Peaked cut $C_{8-0}E_6$ as described hereinbefore.

Thickeners are desirable additives, for both spray and non-spray products. The thickeners are preferably those described in U.S. Pat. No. 5,232,632, Woo et al., at the levels described in said patent, said patent being incorporated herein by reference.

What is claimed is:

1. Nonionic detergent surfactant which is an ethoxylated alcohol in which the alcohol contains an alkyl group containing from six to eleven carbon atoms and in which there are from about three to about twelve ethoxy moieties in a peaked distribution such that at least about 70% and less than about 95% of the molecules by weight have an ethoxy content within about two ethoxy moieties of the average ethoxy content.

2. Nonionic detergent suffactant which is an ethoxylated alcohol in which the alcohol contains an alkyl group containing from six to eleven carbon atoms and in which there are from about three to about twelve ethoxy moieties in a peaked distribution such that at least about 80% and less than about 95% of the molecules by weight have an ethoxy content within about two ethoxy moieties of the average ethoxy content.

* * * * *